United States Patent
Barjatia et al.

(10) Patent No.: US 10,289,434 B2
(45) Date of Patent: *May 14, 2019

(54) SEQUENTIAL ACTIVITY INTELLIGENT PERSONAL ASSISTANT

(71) Applicant: HARMAN INTERNATIONAL INDUSTRIES, INCORPORATED, Stamford, CT (US)

(72) Inventors: Meenakshi Barjatia, Salt Lake City, UT (US); James M. Kirsch, Salt Lake City, UT (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/044,225

(22) Filed: Jul. 24, 2018

(65) Prior Publication Data
US 2019/0095228 A1 Mar. 28, 2019

Related U.S. Application Data

(63) Continuation of application No. 15/712,659, filed on Sep. 22, 2017, now Pat. No. 10,048,973.

(51) Int. Cl.
| | |
|---|---|
| *H04R 29/00* | (2006.01) |
| *G06F 9/451* | (2018.01) |
| *G06N 3/02* | (2006.01) |
| *H04R 19/04* | (2006.01) |
| *G06F 17/21* | (2006.01) |

(52) U.S. Cl.
CPC ............ *G06F 9/453* (2018.02); *G06F 17/21* (2013.01); *G06N 3/02* (2013.01); *H04R 19/04* (2013.01); *H04R 29/004* (2013.01); *H04R 2430/20* (2013.01)

(58) Field of Classification Search
CPC ..................................................... H04R 29/00
See application file for complete search history.

(56) References Cited

U.S. PATENT DOCUMENTS

| | | | | |
|---|---|---|---|---|
| 5,831,936 | A | * 11/1998 | Zlotnick | ............... G01S 3/801 367/124 |
| 9,799,329 | B1 | * 10/2017 | Pogue | ................... G10L 15/20 |
| 2006/0184369 | A1 | 8/2006 | Levonas | |
| 2007/0189128 | A1 | 8/2007 | Chung | |

(Continued)

*Primary Examiner* — Olisa Anwah
(74) *Attorney, Agent, or Firm* — Brooks Kushman P.C.

(57) ABSTRACT

An audio processor receives ambient audio input and performs time frequency analysis. A controller receives a first description of a first step of a project, generates a first sound signature according to the time frequency analysis of the ambient audio input during a timeframe corresponding to performance of the first step, adds the first step to a project script including the first description and the first signature for matching to future audio input to determine whether the first step is being performed, receives a second description of a second step of the project, generates a second sound signature based on the time frequency analysis of the ambient audio input during a timeframe corresponding to performance of the second step, and adds the second step to the project script including the second description and the second signature for matching to future audio input to determine whether the second step is performed.

16 Claims, 3 Drawing Sheets

(56) References Cited

U.S. PATENT DOCUMENTS

| | | | |
|---|---|---|---|
| 2010/0142715 A1* | 6/2010 | Goldstein | G06F 17/30743 |
| | | | 381/56 |
| 2013/0302768 A1 | 11/2013 | Webb | |
| 2015/0098575 A1 | 4/2015 | Kulavik et al. | |
| 2015/0104023 A1 | 4/2015 | Bilobrov | |
| 2017/0195810 A1* | 7/2017 | Gonzales, Jr. | G07C 5/0808 |

* cited by examiner

SEQUENTIAL ACTIVITY INTELLIGENT PERSONAL ASSISTANT

CROSS-REFERENCE TO RELATED APPLICATIONS

This application is a continuation of U.S. application Ser. No. 15/712,659 filed Sep. 22, 2017, now U.S. Pat. No. 10,048,973 issued Aug. 14, 2018, the disclosure of which is hereby incorporated in its entirety by reference herein.

TECHNICAL FIELD

Aspects of the disclosure generally relate to a personal assistant for use in performing sequential activities having a plurality of distinct steps.

BACKGROUND

Many types of project require a sequence of steps to be performed. For instance, a recipe can include a listing of operations to be performed to make a particular dish of food. A cookbook lists the sequence of steps of the recipe, but gives no indication to the reader whether a step has been completed. When a user attempts to cook the dish using the recipe, it can be distracting and time-consuming for the user to repeatedly go back to the recipe and check what the next step is. This can also cause mishaps such as overcooking or burning while consulting the cookbook.

Electronic systems that instruct a user may require user input to control the system. For instance, a user may review an online video of performance of a sequence of steps, but may have to pause and rewind the video multiple times to follow along when performing the steps his or herself. These systems may cause difficulties for a user who has not completed the project before, as the user must perform the steps of the task and also provide user input to the electronic system to keep track of the directions. This switching between the task and the directions for the task interrupts the ability of the user to performing the required steps correctly and efficiently.

SUMMARY

In one or more illustrative embodiments, a non-transitory storage maintains a project script including a sequence of steps, each step including a description of the step and a sound signature indicative of ambient sounds that occur during performance of the step. An audio processor is programmed to receive ambient audio input and perform a time frequency analysis of the ambient audio input. A controller is programmed to provide a description of a next step of the project script upon completion of a current step identified responsive to the time frequency analysis of the ambient audio input matching a sound signature corresponding to the next step of the project script.

In one or more illustrative embodiments, an audio processor is programmed to receive ambient audio input and perform time frequency analysis of the ambient audio input. A controller is programmed to receive a first description of a first step of a project, generate a first sound signature according to the time frequency analysis of the ambient audio input during a timeframe corresponding to performance of the first step, and add the first step to a project script including the first description and the first sound signature. The controller is also programmed to receive a second description of a second step of the project, generate a second sound signature based on the time frequency analysis of the ambient audio input during a timeframe corresponding to performance of the second step, and add the second step to the project script including the second description and the second sound signature.

In one or more illustrative embodiments, a method includes receiving audio input indicative of a request to perform guided instruction of a project script having a sequence of steps, each step including a description of the respective step and a sound signature indicative of ambient sounds that occur during performance of the respective step; providing an audio output indicating a description of a first step of the project script; performing a time frequency analysis of ambient audio input responsive to providing the audio output; and providing a description of a next step of the project script responsive to the time frequency analysis of the ambient audio input matching a sound signature corresponding to the next step of the project script.

DETAILED DESCRIPTION

Figure 1:
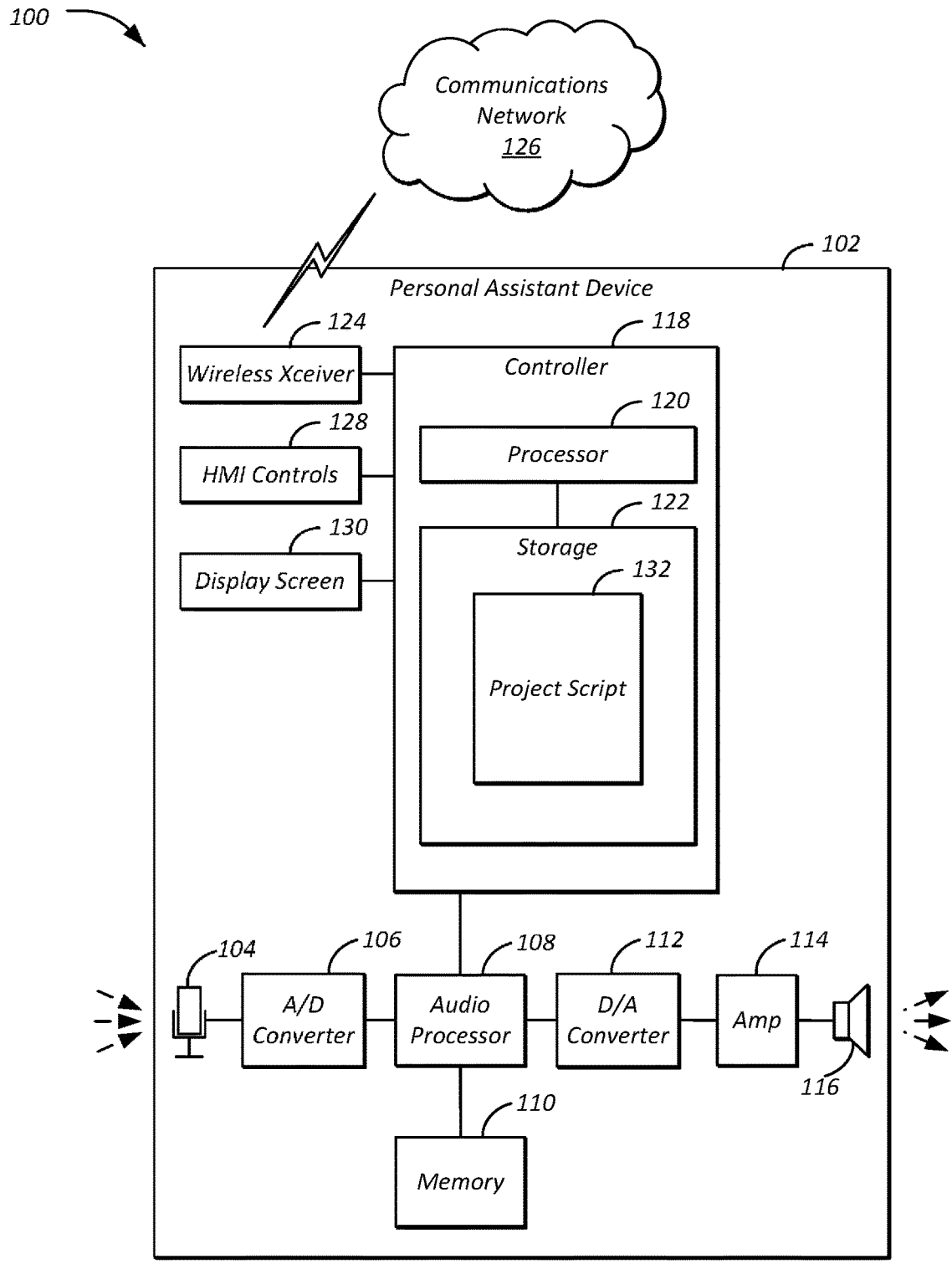
FIG. 1 illustrates a system including an example intelligent personal assistant device, in accordance with one or more embodiments.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The aspects of the present disclosure generally relate to an intelligent personal assistant device that provides guided instruction to a user for a project requiring the performance of sequential activities. The intelligent personal assistant device may use a project script that describes the set of steps for the performance of the project, where each step of the project script is associated with a corresponding sound signature. The intelligent personal assistant device utilizes a microphone or other audio input device to create an acoustic signal descriptive of audio surrounding of the intelligent personal assistant device. The intelligent personal assistant device further utilizes a signal processing/machine learning system to identify the previous and current actions of the user. For instance, the activity being performed by the user may be detected based on the structure of the acquired acoustic signal. Artificial Intelligence (AI) may be used to analyze and classify the sound events. Once classified, the intelligent personal assistant device can locate their position in the sequence of actions of the project by comparison to the sound signatures of the project script. In another example, the position of the activity may be located by using information about the preceding activities, which may be helpful in resolving acoustically-similar activities. Based on the location of the user in the sequence of actions of the project, the intelligent personal assistant device may instruct the user regarding the next steps in the project. For instance, if the intelligent personal assistant device identifies per the acoustic signal that one step of a project is complete, the intelligent personal assistant device may utilize that identification as a trigger to instruct the user regarding the next steps. Additionally, the intelligent personal assistant device may allow for manual indications by the user that a step is completed, such as by receiving voice input from the user indicating the current step has been completed. Accordingly, the intelligent personal assistant device may allow a user to learn a new skill, such as cooking, or help in developing or maintaining an activity, such as working out.

The intelligent personal assistant device may further allow a user to create new project scripts to guide users in performing additional tasks. For instance, a user may record a sequence of steps and associate the steps with sound signatures characteristics of performance of those steps. In some cases, the sound signatures may be captured during recording of the task, while in other cases, the sound signatures may be prerecorded and/or assigned to the tasks after recording. By allowing for the saving of additional project scripts, the intelligent personal assistant device can be taught to perform guided instruction to users for a wide variety of projects. Further aspects of the disclosure are discussed in further detail below.

FIG. 1 illustrates a system 100 including an example intelligent personal assistant device 102. The personal assistant device 102 receives audio through a microphone 104 or other audio input, and passes the audio through an analog to digital (A/D) converter 106 to be identified or otherwise processed by an audio processor 108. The audio processor 108 also generates speech or other audio output, which may be passed through a digital to analog (D/A) converter 112 and amplifier 114 for reproduction by one or more loudspeakers 116. The personal assistant device 102 also includes a controller 118 connected to the audio processor 108 and configured to manage the guided instructions for a project according to a project script 132. Based on the identification of the input audio by the audio processor 108, the controller 118 determines the current status of the user within the project script 132, and directs the audio processor 108 to generate prompts indicative of the next steps to progress through the project script 132. The controller 118 also interfaces with a wireless transceiver 124 to facilitate communication of the personal assistant device 102 with a communications network 126, such as to receive additional project scripts 132. In many examples, the controller 118 also is connected to one or more Human Machine Interface (HMI) controls 128 to receive user input, as well as a display screen 130 to provide visual output. It should be noted that the illustrated system 100 is merely an example, and more, fewer, and/or differently located elements may be used.

The A/D converter 106 receives audio input signals from the microphone 104. The A/D converter 106 converts the received signals from an analog format into a digital signal in a digital format for further processing by the audio processor 108.

While only one is shown, one or more audio processors 108 may be included in the personal assistant device 102. The audio processors 108 may be one or more computing devices capable of processing audio and/or video signals, such as a computer processor, microprocessor, a digital signal processor, or any other device, series of devices or other mechanisms capable of performing logical operations. The audio processors 108 may operate in association with a memory 110 to execute instructions stored in the memory 110. The instructions may be in the form of software, firmware, computer code, or some combination thereof, and when executed by the audio processors 108 may provide the audio recognition and audio generation functionality of the personal assistant device 102. The instructions may further provide for audio cleanup (e.g., noise reduction, filtering, etc.) prior to the recognition processing of the received audio. The memory 110 may be any form of one or more data storage devices, such as volatile memory, non-volatile memory, electronic memory, magnetic memory, optical memory, or any other form of data storage device. In addition to instructions, operational parameters and data may also be stored in the memory 110, such as a phonetic library for the creation of speech from textual data.

The D/A converter 112 receives the digital output signal from the audio processor 108 and converts it from a digital format to an output signal in an analog format. The output signal may then be made available for use by the amplifier 114 or other analog components for further processing.

The amplifier 114 may be any circuit or standalone device that receives audio input signals of relatively small magnitude, and outputs similar audio signals of relatively larger magnitude. Audio input signals may be received by the amplifier 114 and output on one or more connections to the loudspeakers 116. In addition to amplification of the amplitude of the audio signals, the amplifier 114 may also include signal processing capability to shift phase, adjust frequency equalization, adjust delay or perform any other form of manipulation or adjustment of the audio signals in preparation for being provided to the loudspeakers 116. For instance, the loudspeakers 116 can be the primary medium of instruction when the device 102 has no display screen 130 or the user desires interaction that does not involve looking at the device. The signal processing functionality may additionally or alternately occur within the domain of the audio processor 108. Also, the amplifier 114 may include capability to adjust volume, balance and/or fade of the audio signals provided to the loudspeakers 116. In an alternative example, the amplifier 114 may be omitted, such as when the loudspeakers 116 are in the form of a set of headphones, or when the audio output channels serve as the inputs to another audio device, such as an audio storage device or a further audio processor device. In still other examples, the loudspeakers 116 may include the amplifier 114, such that the loudspeakers 116 are self-powered.

The loudspeakers 116 may be of various sizes and may operate over various ranges of frequencies. Each of the loudspeakers 116 may include a single transducer, or in other cases multiple transducers. The loudspeakers 116 may also be operated in different frequency ranges such as a subwoofer, a woofer, a midrange and a tweeter. Multiple loudspeakers 116 may be included in the personal assistant device 102.

The controller 118 may include various types of computing apparatus in support of performance of the functions of the personal assist device 102 described herein. In an example, the controller 118 may include one or more processors 120 configured to execute computer instructions, and a storage medium 122 on which the computer-executable instructions and/or data may be maintained. A computer-readable storage medium (also referred to as a processor-readable medium or storage 122) includes any non-transitory (e.g., tangible) medium that participates in providing data (e.g., instructions) that may be read by a computer (e.g., by the processor(s) 120). In general, a processor 120 receives instructions and/or data, e.g., from the storage 122, etc., to a memory and executes the instructions using the data, thereby performing one or more processes, including one or more of the processes described herein. Computer-executable instructions may be compiled or interpreted from computer programs created using a variety of programming languages and/or technologies including, without limitation, and either alone or in combination, Java, C, C++, C#, Assembly, Fortran, Pascal, Visual Basic, Python, Java Script, Perl, PL/SQL, etc.

As shown, the controller 118 may include a wireless transceiver 124 or other network hardware configured to facilitate communication between the controller 118 and other networked devices over the communications network 126. As one possibility, the wireless transceiver 124 may be a cellular network transceiver configured to communicate data over a cellular telephone network. As another possibility, the wireless transceiver 124 may be a Wi-Fi transceiver configured to connect to a local-area wireless network to access the communications network 126.

The controller 118 may receive input from human-machine interface (HMI) controls 128 to provide for user interaction with personal assistant device 102. For instance, the controller 118 may interface with one or more buttons or other HMI controls 128 configured to invoke functions of the controller 118. The controller 118 may also drive or otherwise communicate with one or more displays 130 configured to provide visual output to users, e.g., by way of a video controller. In some cases, the display 130 may be a touch screen further configured to receive user touch input via the video controller, while in other cases the display 130 may be a display only, without touch input capabilities.

Figure 2:
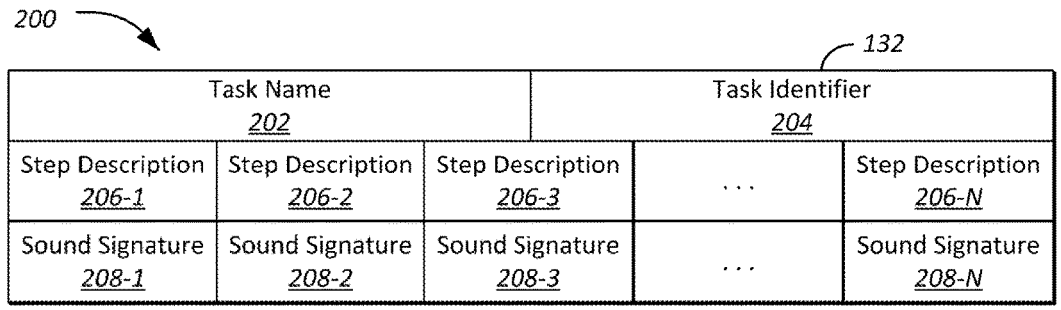
FIG. 2 illustrates an example project script, in accordance with one or more embodiments

As discussed in detail with respect to FIG. 2, the project script 132 describes a set of steps for the performance of a project. The current status indicates what step of the project script 132 is the current step awaiting performance by the user.

Referring to FIG. 2, an example project script 132 includes a project name 202, a project identifier 204, and a sequence of step descriptions 206-1 through 206-N (collectively 206) with corresponding sound signatures 208-1 through 208-N (collectively 208). Generally, each step includes a description 206 indicating the operation or operations to be performed by the user to complete the step. Each step also includes a sound signature 208 indicative of sounds that would be observed during performance of the corresponding step.

More specifically, the project name 202 that may be used to identify the project to a user in a user interface of the personal assistant device 102. In an example, when the project script 132 is being performed, the project name 202 may be provided to the display screen 130 of the personal assistant device 102. In another example, the project name 202 may be spoken by the user to select guided performance of the project script 132 by the personal assistant device 102.

The project identifier 204 may be a unique number or other identifier of the project that may be used to identify the project script 132 to computing devices such as the personal assistant device 102. The project identifier 204 may be useful in cases where different projects have the same or a similar project name 202.

The step descriptions 206 may each indicate information about a particular step in the sequence of the project. For instance, a step description 206 may describe what operations are to be performed by the user in the corresponding step. In some cases, the information of the step description 206 may be provided to the user audibly by the audio processor 108. For instance, the audio processor 108 may provide simulated speech to be reproduced by the loudspeakers 116. This may allow the user to concentrate on the project without requiring use of the user's hands or eyes. In other cases, the information may additionally or alternately be provided to the display screen 130 of the personal assistant device 102.

Each step description 206 of the project script 132 may also have a corresponding sound signature 208. The corresponding sound signature 208 may indicate a frequency signature of the expected audio to be captured during performance of the corresponding step. In an example, the sound signature 208 may include data indicative of expected frequencies and amplitudes that, when received, would indicate that the corresponding step of the project script 132 is being performed. For instance, running water may have a first sound signature 208, while sizzling of vegetables in a pan may have a second different sound signature 208. It should be noted that the sound signature 208 may itself include a sequence of sounds, e.g., that repeat in a cycle. For instance, while chopping vegetables, the sound signature 208 may include information indicative of brief silence or a low amplitude activity, followed by the sound of knife hitting the board, followed by a silence again, and so on.

Variations on the example project script 132 are possible. For instance, in some examples the project script 132 may include one or more steps that may be accomplished in parallel. As another example, the project script 132 may include one or more steps that may be required to be performed periodically while a sequence of other steps is to be performed. One example of such a periodic step may be to stir a sauce periodically while other operations are being performed.

Figure 3:
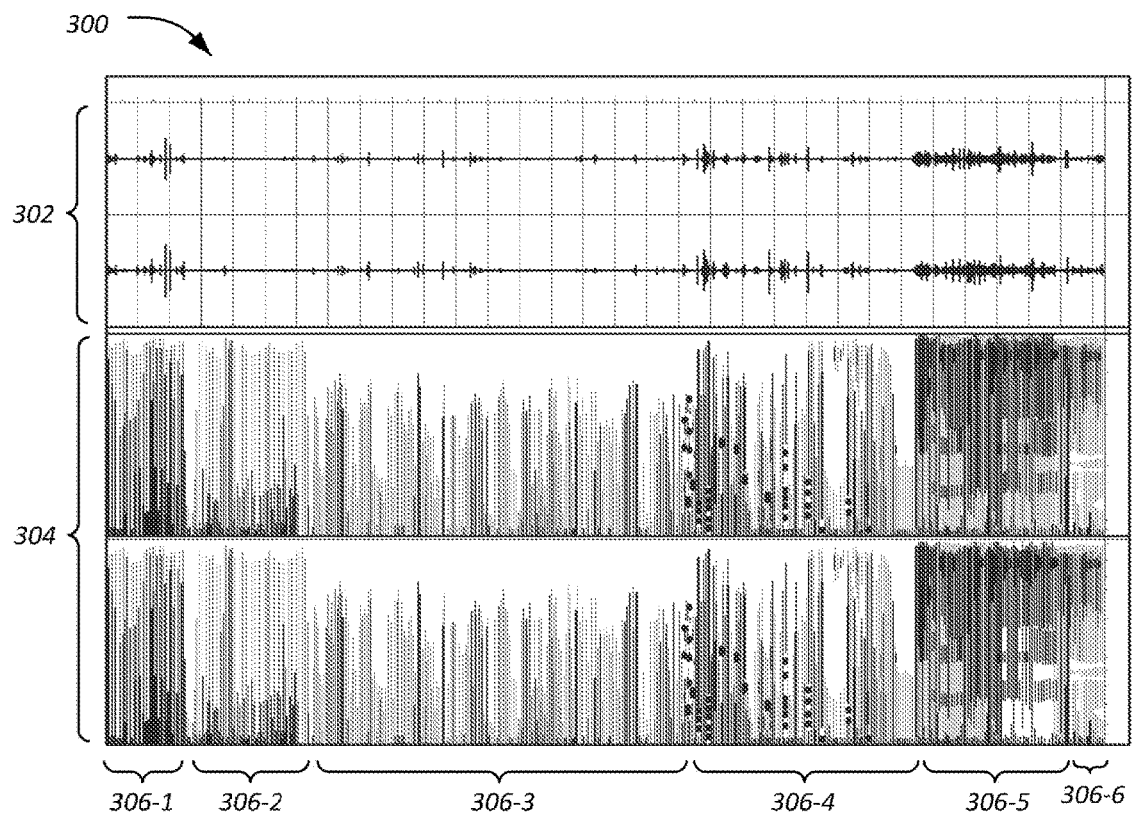
FIG. 3 illustrates an example illustrating audio input in relation to steps of a project script, in accordance with one or more embodiments.

FIG. 3 illustrates an example 300 illustrating audio input in relation to steps of a project script 132. For instance, the audio input may be received by the microphone 104 of the personal assistant device 102 for processing by the audio processor 108. The illustrated example 300 includes a waveform 302 of received audio during performance of a plurality of steps of a project script 132, as well as a corresponding time frequency analysis 304 of the frequencies during the steps.

As shown, the horizontal axis of the waveform 302 represents time, while the vertical axis represents amplitude. Also as shown, the horizontal axis of the time frequency analysis 304 represents time, the vertical axis represents frequency, and the amplitude of a particular frequency at a particular time is represented by an intensity or color of each point in the image. Notably, the waveform 302 shows minimal difference in amplitude between certain steps of the project script 132, although large changes of amplitude may be seen in certain other steps. While it may be possible to use amplitude/energy/power difference alone to classify among some type of tasks, this scheme may fail for other types of tasks. Time frequency analysis 304 provides additional information about the pattern of change in the frequency domain over time, and therefore, the time frequency analysis 304 shows more significant difference between the steps. Thus, it can be seen that use of a time frequency analysis of the input sound provides an additional dimension of information with respect to determining the content of the received audio input.

In the specific example 300, a cooking project is shown having a plurality of steps 306. The steps of the project include a preparation step 306-1 (e.g., getting out containers and vegetable items cook), a washing the vegetables step 306-2, a chopping the vegetables step 306-3, a popping of spices when entering a pan step 306-4, a sizzling of onions in the pan step 306-5, and a recognition that the onions are cooked step 306-6. Each of these steps 306 can be seen to have different time frequency content. For instance, the washing step 306-2 has a uniform broadband noise type of distribution of frequency content, the popping step 306-4 has short bursts of high intensity content, the sizzling onions step 306-5 has a distribution of intense high frequency content, and the onions complete step 306-6 may has a similar distribution but with less intense high frequency content.

Based on the structure of the acoustic signal acquired by the audio processor 108 via the microphone 104, the controller 118 of the personal assistant device 102 may detect the activities being performed by the user. The audio processor 108 may utilize a frequency domain decomposition technique to process the received audio. For instance, the audio processor 108 may utilize a Fast Fourier Transform (FFT) process on digitized microphone 104 audio received to the audio processor 108. The audio processor 108 may sample the received data in the time domain, broken up into portions (which may overlap), and perform Fourier transforms on the portions to calculate the magnitude of the frequency spectrum for each portion. Each portion may correspond to a measurement of magnitude versus frequency for a specific moment in time of the input (i.e., the midpoint of the portion). These spectrums or time plots may then be combined to form an overall time frequency representation of the frequencies and amplitudes of the detected audio (in some cases being slightly overlapped using windowing techniques if the portions overlap). This representation may then be compared to the sound signatures 208 of the project script 132 to identify the location of the user in the sequence of actions of the project of the project script 132. It should be noted that use of FFT is only one example, and other techniques to decompose a signal into its frequency components could be used, such as discrete cosine formation (DCT) or discrete Fourier transformation (DFT).

As another possibility, the audio processor 108 may be programmed to generate the time frequency analysis by utilizing filter banks to break down the audio received to the audio processor 108 into frequency components. As yet a further possibility, the audio processor 108 may be programmed to generate the time frequency analysis by utilizing a neural network to extract frequency component features from the audio input.

When a sound signature 208 of a specific step of the project script 132 is identified, the personal assistant device 102 may instruct the user regarding the next step in the sequence of the project script 132. For instance, if the intelligent personal assistant identifies, according to the acoustic signal, that one step of a project is complete, the intelligent personal assistant may utilize that identification as a trigger to instruct the user regarding the next step.

It should be noted that in some examples, stereo or multi-channel audio may be received and processed by the personal assistant device 102. For instance, the microphone 104 of the personal assistant device 102 may be a stereo microphone device including multiple elements configured to receive audio signals with different directivity. As another possibility, microphone 104 of the personal assistant device 102 may include an array of elements that utilize beam-forming algorithms to locate where a sound is coming from to aid in determining what the sound may be. In such an example, the personal assistant device 102 may analyze the spatial information of the received audio signals to determine whether received sounds at a location indicative of a trigger to instruct the user regarding a next step. For instance, the personal assistant device 102 may confirm that cooking sounds are emanating from a location at which the cooking project is being performed.

It should also be noted that other examples of sequential projects apart from cooking may be performed using the personal assistant device 102. In another example, a project script 132 may be utilized by a user while performing a fitness routine. For instance, if the user is performing cross-fit, the personal assistant device 102 may monitor breathing rate (e.g., by panting sounds), the type of activity (e.g., jumping jacks vs. box jumps), speed of activity, etc., and may push the user to continue the current step or move to the next step of the routine by giving suggestions according to the observed sounds.

Figures 4, 5:
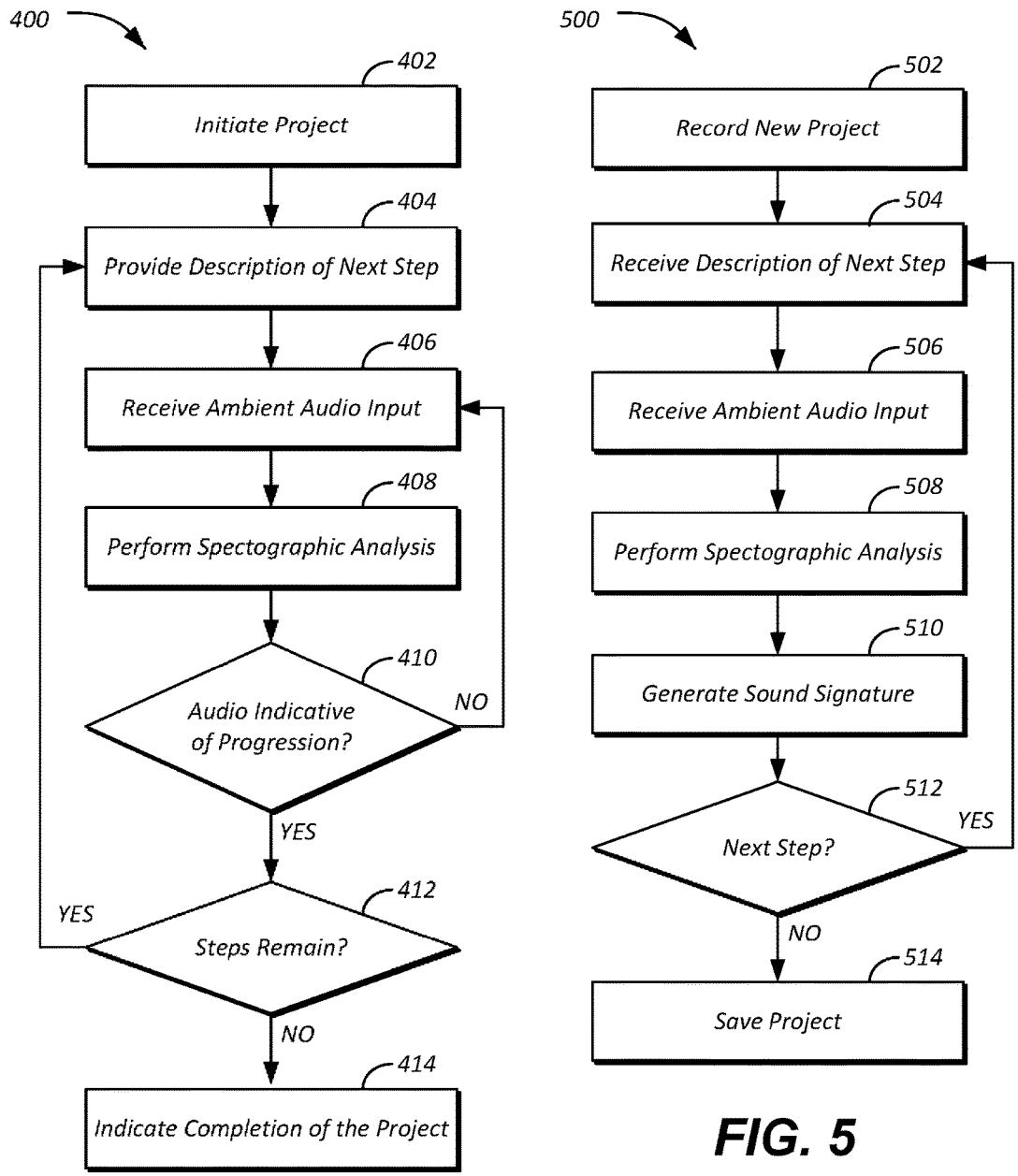
FIG. 4 illustrates an example process for guided instruction of a project script having a sequence of steps.
FIG. 5 illustrates an example process for creation of a project script.

FIG. 4 illustrates an example process 400 for guided instruction of a project having a sequence of steps. In an example, the process 400 may be performed by the personal assistant device 102 guiding the user through performance of a project script 132.

At operation 402, the personal assistant device 102 initiates a project. In an example, the user may direct the personal assistant device 102 to start a project by speaking the project name 202 of a project stored to the storage 122 of the personal assistant device 102. In the request, the microphone 104 of the personal assistant device 102 captures analog audio of the surroundings of the personal assistant device 102, which is converted to a digital via the A/D converter 106, and provided to the audio processor 108. The audio processor 108 and/or controller 118 then converts the audio into text, which is processed as a command by the controller 118. In another example, the audio processor 108 provides the audio to the controller 118, which in turn provides the audio to a speech recognition engine connected to the communications network 126 by use of the wireless transceiver 124. The speech recognition server then provides the recognized speech to the personal assistant device 102, which identifies the project script 132 to be run. In yet a further example, the command sent to the speech recognition server causes the speech recognition server to send the project script 132 to be run to the personal assistant device 102. The personal assistant device 102 may further initiate the current status to the first step of the project script 132.

At 404, the personal assistant device 102 provides a description of the next step of the project. In an example, the controller 118 may direct the audio processor 108 to synthesize a voice prompt for the step description 206 of the step of the project script 132 indicated by the current status. Additionally or alternately, the controller 118 may display the step description 206 to the display screen 130 of the personal assistant device 102.

The personal assistant device 102 receives ambient audio input at 406. In an example, the microphone 104 of the personal assistant device 102 captures analog audio of the surroundings of the personal assistant device 102, which is converted to a digital via the A/D converter 106, and provided to the audio processor 108.

At operation 408, the personal assistant device 102 performs time frequency analysis of the received audio input. In an example, the audio processor 108 samples the received data to calculate the magnitude of the frequency spectrum for the received audio.

At 410, the personal assistant device 102 determines whether the analyzed audio is indicative of progression in the project. In an example, the audio processor 108 compares the sampled data to the sound signatures 208 of the projects of the project script 132. The audio processor 108 and/or controller 118 determines whether the analyzed audio matches to the sound signature 208 of the current step or to the sound signature 208 of a further step of the project script 132.

In some examples, the comparison of the analyzed audio matches to the sound signatures 208 may include one or more of pattern recognition, machine learning, artificial intelligence and digital signal processing (DSP) processes such as: Spectral Analysis, Clustering/Classification Algorithms, Support Vector Machines (SVMs), Bayesian networks, or probability of sequence algorithms such as Hidden Markov Models (HMMs). Classification algorithms, such as pattern recognition, clustering, SVMs, Neural networks, etc. can be used for identification of the current task that is being performed based on the recorded audio. Algorithms such as HMMs and Recurrent Neural Networks (RNNs) can also be used to recognize a probabilistic sequence of sound 208 signatures that may comprise a single task or step.

For instance, a pattern recognition system may include a training phase during which reference sound signatures 208 are preprocessed (e.g., filtering, noise reduction, etc.), features of the preprocessed audio are extracted, and the existence of absence of these features is learned as being likely of the audio condition. Once the learning is performed, the learned signature may be used for classification of the audio input to determine whether the audio matches the reference sound signature 208. For instance, the classification may include preprocessing of the audio input, providing of the preprocessed input to a feature extraction phase, and classification of the audio as matching the reference sound signatures 208 or not according to the learned patterns.

As another possibility, clustering algorithms may be used to classify the analyzed audio in comparison to the sound signatures 208. For instance, one or more aspects of the analyzed audio that can be provided a value along a dimension may be extracted (e.g., level of frequency content within various frequency bands), and placed in a dimensional space according to those values. Then, analyzed audio that is less than a threshold clustering distance from the sound signature 208 may be considered to be a match to that sound signature 208, while sound signatures 208 with a greater distance are considered not to be matches.

In other examples, the user may be able to provide direct feedback that a step has been complete. In an example, the user may provide affirmative input to the device 102 that the step is complete (e.g., "I'm done chopping vegetables", "I'm ready for the next step," etc.). In such an example, the audio processor 108 may perform speech to text on the received input. The audio processor 108 may then indicate the text to the controller 118 to cause the controller 118 to identify that a next step is warranted.

If the analyzed audio matches to the current step, control passes to operation 406. If, however, the audio matches a sound signature 208 of a further step or the user provides explicit instruction to proceed, control passes to operation 412.

At 412, the personal assistant device 102 determines whether steps remain in the project. In an example, the controller 118 may access the project script 132 to determine whether additional steps beyond the current step exist in the project script 132. In some cases, the final step of the project script 132 may include a sound signature 208 indicative of completion of the project with no further description 206. If there are further steps, the controller 118 advances the current status to that of the step matched by the sound signature 208 and passes control to operation 404. If no further steps exist in the project script 132, control passes to operation 414.

The personal assistant device 102 indicates completion of the project at 414. In an example, the personal assistant device 102 may synthesize a voice prompt indicating that the project is completed. Additionally or alternately, the controller 118 may display to the display screen 130 of the personal assistant device 102 an indication that the project is completed. After operation 414, the process 400 ends.

FIG. 5 illustrates an example process 500 for creation of a project script 132. In an example, the process 500 may be performed by the personal assistant device 102 receiving steps of a new project script 132 from a user. It should be noted that a project script 132 may be created via a different personal assistant device 102 than the one that later executes the steps of the project. For instance, a user may upload the project script 132 to a remote server to allow other devices to download the project script 132. It is possible that the different personal assistant devices 102 and the other devices may be owned and used by other users possibly in other geographical locations.

At operation 502, the personal assistant device 102 starts a new project. In an example, the user provides voice input to the personal assistant device 102 indicating that a new project script 132 is being created. For instance, the microphone 104 of the personal assistant device 102 captures analog audio of the user speaking, which is converted to a digital via the A/D converter 106, and provided to the audio processor 108. The audio processor 108 and/or controller 118 then converts the audio into speech, and extract that a new project script 132 is to be created from the speech. Additionally or alternately, a project name 202 may be extracted from the speech as well.

At operation 504, the personal assistant device 102 receives a description of the next step. In an example, the microphone 104 of the personal assistant device 102 may further capture audio of the user speaking, which is translated by the audio processor 108 and/or controller 118 into a step description 206 of a next step of the project script 132 (or a first step if this is the initiation of creation of the project script 132).

At operation 506, and similar to as discussed above with respect to operation 406, the personal assistant device 102 receives ambient audio input. At operation 508, and similar to as discussed above with respect to operation 408, the personal assistant device 102 performs time frequency analysis of the ambient audio input.

At operation 510, the personal assistant device 102 generates a sound signature 208. In an example, the controller 118 creates the sound signature 208 corresponding to the step description 206 based on the time frequency analysis of the ambient audio input determined at operation 506. This sound signature 208 may accordingly be matched to future audio input to determine whether the step is currently being performed. It should be noted that in some examples, recordings of new signatures can be a separate act from recording a new project script 132. For instance, regardless of whether the project script 132 is one that is received from a remote server or is learned by the device 102 itself, a new signature may be applied to an existing step of a project script 132 to refine classification for that step. Or, even if a new task is being recorded, an existing sound signature can be selected and applied to the step of the project script 132.

At operation 512, the personal assistant device 102 determines whether there is a next step for the project. In an example, the personal assistant device 102 may receive further voice input from the user indicating that a next step is to be begun. If so, control returns to operation 504. In another example, the personal assistant device 102 may receive further voice input from the user indicating that the project is completed. If so, control passes to operation 514.

At operation 514, the personal assistant device 102 saves the project. In an example, the personal assistant device 102 stores the project script 132 to the storage 122 of the personal assistant device 102. Additionally or alternately, the personal assistant device 102 stores the project script 132 to a remote server configured to host project scripts 132. After operation 514, the process 500 ends.

Computing devices described herein, such as the audio processors 108 and controller 118 of the personal assistant device 102, generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, JavaScript, C, C++, C#, Visual Basic, Java Script, Python, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

With regard to the processes, systems, methods, heuristics, etc., described herein, it should be understood that, although the steps of such processes, etc., have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A system for recording sequential activities having a plurality of distinct steps comprising:
    an audio processor programmed to receive ambient audio input and perform time frequency analysis of the ambient audio input; and
    a controller programmed to
        receive a first description of a first step of a project responsive to the ambient audio input being processed to text via the audio processor,
        generate a first sound signature according to the time frequency analysis of the ambient audio input during a timeframe corresponding to performance of the first step,
        add the first step to a project script including the first description and the first sound signature for matching to future audio input to determine whether the first step is currently being performed,
        receive a second description of a second step of the project responsive to the ambient audio input being processed to text via the audio processor,
        generate a second sound signature based on the time frequency analysis of the ambient audio input during a timeframe corresponding to performance of the second step, and
        add the second step to the project script including the second description and the second sound signature for matching to future audio input to determine whether the second step is currently being performed.

2. The system of claim 1, further comprising a wireless transceiver, wherein the controller is further programmed to direct the wireless transceiver to send the project script over a communications network to a remote server for storage.

3. The system of claim 1, wherein the audio processor is programmed to generate the time frequency analysis by utilizing a Fast Fourier Transform (FFT) process in the time domain.

4. A system for recording sequential activities having a plurality of distinct steps comprising:
    an audio processor programmed to receive ambient audio input and perform time frequency analysis of the ambient audio input; and
    a controller programmed to
        receive a first description of a first step of a project,
        generate a first sound signature according to the time frequency analysis of the ambient audio input during a timeframe corresponding to performance of the first step,
        add the first step to a project script including the first description and the first sound signature for matching to future audio input to determine whether the first step is currently being performed,
        receive a second description of a second step of the project,
        generate a second sound signature based on the time frequency analysis of the ambient audio input during a timeframe corresponding to performance of the second step,
        add the second step to the project script including the second description and the second sound signature for matching to future audio input to determine whether the second step is currently being performed,
        receive a project name for the project responsive to the audio input being processed to text via the audio processor, and
        assign the project name to the project script.

5. The system of claim 1, wherein the controller is further programmed to capture the ambient audio input during recording of the project.

6. The system of claim 1, wherein the first sound signature is prerecorded prior to recording of the project, and the controller is further programmed to receive selection of the first sound signature to apply the first sound signature to the first step.

7. The system of claim 1, wherein the first sound signature includes a sequence of sounds that repeat in a cycle.

8. The system of claim 1, wherein the ambient audio input includes a plurality of input channels, and wherein the controller is further programmed to analyze spatial information of the plurality of input channels to identify a location at which the ambient audio input is emanating.

9. A method for recording sequential activities having a plurality of distinct steps comprising:
receiving a first description of a first step of a project;
generating a first sound signature according to time frequency analysis of ambient audio input during a timeframe corresponding to performance of the first step;
adding the first step to a project script including the first description and the first sound signature for matching to future audio input to determine whether the first step is currently being performed;
receiving a second description of a second step of the project;
generating a second sound signature based on the time frequency analysis of the ambient audio input during a timeframe corresponding to performance of the second step; and
adding the second step to the project script including the second description and the second sound signature for matching to future audio input to determine whether the second step is currently being performed,
wherein one or more of a project name assigned to the project script, the first description, and the second description are received responsive to the audio input being processed to text via an audio processor receiving ambient audio input and performing time frequency analysis of the ambient audio input.

10. The method of claim 9, further comprising sending the project script over a communications network to a remote server for storage.

11. The method of claim 9, further comprising generating the time frequency analysis by utilizing a Fast Fourier Transform (FFT) process in the time domain.

12. The method of claim 9, further comprising capturing the ambient audio input during recording of the project.

13. The method of claim 9, wherein the first sound signature is prerecorded prior to recording of the project, and further comprising receiving a selection of the first sound signature to apply the first sound signature to the first step.

14. The method of claim 9, wherein the first sound signature includes a sequence of sounds that repeat in a cycle.

15. The method of claim 9, wherein the ambient audio input includes a plurality of input channels, and further comprising analyzing spatial information of the plurality of input channels to identify a location at which the ambient audio input is emanating.

16. A non-transitory computer-readable medium comprising instructions that, when executed by a processor of a device for recording sequential activities having a plurality of distinct steps, cause the device to:
receive a first description of a first step of a project responsive to audio input being processed to text via an audio processor receiving ambient audio input and performing time frequency analysis of the ambient audio input;
generate a first sound signature according to time frequency analysis of the ambient audio input during a timeframe corresponding to performance of the first step;
add the first step to a project script including the first description and the first sound signature for matching to future audio input to determine whether the first step is currently being performed;
receive a second description of a second step of the project responsive to the audio input being processed to text via the audio processor;
generate a second sound signature based on the time frequency analysis of the ambient audio input during a timeframe corresponding to performance of the second step;
add the second step to the project script including the second description and the second sound signature for matching to future audio input to determine whether the second step is currently being performed;
receive a project name for the project responsive to the audio input being processed to text via an audio processor receiving ambient audio input and performing time frequency analysis of the ambient audio input; and
assign the project name to the project script.

* * * * *